United States Patent
Tansey (10) Patent No.: US 10,638,946 B2
(45) Date of Patent: May 5, 2020

(54) METHODS FOR DETECTING TRUTH UTILIZING BIOLOGIC DATA

(71) Applicant: Emtee Associates, L.P., Wilmington, DE (US)

(72) Inventor: Michael Anselme Tansey, Hillsborough, NJ (US)

(73) Assignee: EMTEE ASSOCIATES, L.P., Hillsborough, NJ (US)

( * ) Notice: Subject to any disclaimer, the term of this patent is extended or adjusted under 35 U.S.C. 154(b) by 293 days.

(21) Appl. No.: 14/535,662

(22) Filed: Nov. 7, 2014

(65) Prior Publication Data

US 2015/0134264 A1 May 14, 2015

Related U.S. Application Data

(63) Continuation-in-part of application No. 13/373,769, filed on Nov. 30, 2011, now abandoned.
(Continued)

(51) Int. Cl.
*A61B 5/048* (2006.01)
*A61B 5/0484* (2006.01)
(Continued)

(52) U.S. Cl.
CPC ............ *A61B 5/048* (2013.01); *A61B 5/0476* (2013.01); *A61B 5/0484* (2013.01); *A61B 5/0478* (2013.01); *A61B 5/6868* (2013.01)

(58) Field of Classification Search
None
See application file for complete search history.

(56) References Cited

U.S. PATENT DOCUMENTS

| 3,855,998 A | 12/1974 | Hidalgo-Briceno |
| 4,140,997 A | 2/1979 | Brady |

(Continued)

FOREIGN PATENT DOCUMENTS

| EP | 367106 A1 | 6/1990 |
| EP | 375106 A1 | 6/1990 |

(Continued)

OTHER PUBLICATIONS

Tansey Ph.D., Michael A., Tachiki Ph.D., Kenneth H., and Tansey, Jennifer A., Cartography of Consciousness: A Functional Re-Examination of Theta, Alpha, and Beta, Subtle Energies, 1994, vol. 4, pp. 137 and 146.
(Continued)

*Primary Examiner* — Michael R Bloch
(74) *Attorney, Agent, or Firm* — Rita C. Chipperson; Chipperson Law Group, P.C.

(57) ABSTRACT

Systems and methods for detecting truth utilizing biologic data observed during various time periods occurring prior and subsequent to the presentation of a stimulus to a subject and/or prior and subsequent to a volitional action performed by the subject in response to the stimulus. A method for creating a truth or lie scale involving: presenting a stimulus designed to evoke an action to a subject; monitoring a first change in biologic data between a first epoch and a second epoch, the first epoch occurring during presentation of the stimulus, and the second epoch occurring subsequent to presentation of the stimulus; monitoring a second change in biologic data between a second epoch and a third epoch, the third epoch occurring subsequent to the action performed by the subject; and analyzing the monitored data to create the truth or lie scale.

6 Claims, 6 Drawing Sheets

Related U.S. Application Data (60) Provisional application No. 61/459,085, filed on Dec. 7, 2010.

(51) Int. Cl.
*A61B 5/0476* (2006.01)
*A61B 5/0478* (2006.01)
*A61B 5/00* (2006.01)

(56) References Cited

U.S. PATENT DOCUMENTS

| | | |
|---|---|---|
| 4,407,299 A | 10/1983 | Culver |
| 4,498,080 A | 2/1985 | Culver |
| 4,736,751 A | 4/1988 | Gevins et al. |
| 4,883,067 A | 11/1989 | Knispel et al. |
| 4,919,143 A | 4/1990 | Ayers |
| 4,926,969 A | 5/1990 | Wright et al. |
| 4,928,704 A | 5/1990 | Hardt |
| 5,024,235 A | 6/1991 | Ayers |
| 5,406,957 A | 4/1995 | Tansey |
| 5,564,433 A | 10/1996 | Thornton |
| 5,957,859 A * | 9/1999 | Rosenfeld ............ A61B 5/0476 128/898 |

FOREIGN PATENT DOCUMENTS

| | | |
|---|---|---|
| WO | 8303745 A1 | 11/1983 |
| WO | 9405201 A1 | 3/1994 |

OTHER PUBLICATIONS

Libet, B., Cerebral Processes that Distinguish Conscious Experience from Unconscious Mental Function. Principles of Design and Operation of the Brain, J.C. Eccles & O.D. Creutzfeldt, Eds., Pontificia Academiae Scientarium Scripta Varia 78, Oct. 19-24, 1988, pp. 185-202.

Deecke, L., Grozinger, B. and Kornhuber, H.H., Voluntary Finger Movements in Man: Cerebral Potentials and Theory, Biological Cybernetics, 1976, 23, pp. 99-119.

Farwell, Lawrence A., Brain Fingerprinting: A Comprehensive Tutorial Review of Detection of Concealed Information With Event-Related Brain Potentials, Springer, Cognitive Neurodynamics, Feb. 2012, vol. 6, No. 2, pp. 115-154.

Pollina, Dean et al., Facial Skin Surface Temperature Changes During a "Concealed Information" Test, Annals of Biomedical Engineering, vol. 34, No. 7, Jun. 2006, pp. 1182-1189.

Zhao, Min et al., Identifying Concealed Information Using a Wavelet Feature Extraction and Support Vector Machine, Elsevier, Procedia Environmental Sciences vol. 8, 2011, pp. 337-343.

International Search Report and Written Opinion, PCT/US2015/059379, dated Jan. 26, 2016, 11 pp.

* cited by examiner

METHODS FOR DETECTING TRUTH UTILIZING BIOLOGIC DATA

CROSS-REFERENCE TO RELATED APPLICATIONS

This application claims the benefit of and is a continuation-in-part of the U.S. non-provisional patent application entitled "Apparatus and Method for Monitoring, Analyzing, and Utilizing Brainwave and Biologic Data at Transition Points Along the Neurochromometric Sequence Whereby a Stimulus Presented to the Central Nervous System Results in Cognition and Volitional Action", having Ser. No. 13/373,769, filed Nov. 30, 2011, which claims the benefit of the U.S. provisional patent application entitled "Apparatus and Method for Monitoring, Analyzing, and Utilizing Brainwave and Biologic Data at Transition Points Along the Neurochromometric Sequence Whereby a Stimulus Presented to the Central Nervous System Results in Cognition and Volitional Action," having Ser. No. 61/459,085, filed Dec. 7, 2010, both of which are hereby incorporated by reference in their entireties as if fully set forth herein.

COPYRIGHT NOTICE

A portion of the disclosure of this patent document contains material which may be subject to copyright protection. The copyright owner has no objection to the facsimile reproduction by anyone of the patent document or the patent disclosure, as it appears in the Patent and Trademark Office patent file or records, but otherwise reserves all copyright whatsoever.

BACKGROUND OF THE INVENTION

Embodiments of the present invention generally relate to systems and methods for detecting truth utilizing biologic data. More specifically, the present invention relates to systems and methods for detecting truth utilizing biologic data observed during various time periods occurring prior and subsequent to the presentation of a stimulus to a subject and/or prior and subsequent to an action performed by the subject in response to the stimulus.

Within the field of neuroscience, it is a commonly accepted view that the brain sets the stage of behavior in a micro-temporal manner. The requisite brain-biologic correlates for cognitive behavior are functionally matched and sorted according to an evolving cognitive-brain archetype in fractions of a second. These micro-state neural networks, along with stimulus refinement and associative response, define and determine cognition. The reflections and correlates of "mind" are also to be found in the interleaved energies of the brain's orchestration of individual functional manifestation. In simpler terms, brain activation networks in the cerebral cortex repeatedly change the state of coordination among its constituent areas on a sub-second time scale to, in an ongoing manner, enable/inform one's conscious awareness and determine one's cognitive state. As such, alterations of brain activation networks yield functional changes in the cognitive state and hence the state of mind of the individual. These pre-cognitive changes in the brainwave activation of regional neural networks can be observed and/or recorded via changes in the specific brainwave activity to determine the individual's brainwave energy signature. The characteristics of the pre-cognitive aspects of one's biologic and brainwave energy signature is what ultimately informs/enables one's flow of consciousness and one's cognitive state.

Cognition is a term which has traditionally been used to refer to one's first person awareness of one's own flow of indwelling consciousness awareness of self and mind. As such one's cognitive state is understood to include diverse mental processes such as un-verbalized and verbalized thinking, conceiving, perceiving, reasoning, one's awareness of the truth and falsehood of information, and self-verbalizations. It also includes any class of mental "behavior" involving symbolizing, insight, expectancy, complex rule usage, intentionality, problem solving, and imagery. When one attends to one's cognitive state/flow of consciousness, one is then amenable to internal acknowledgment, critique, self-assessment as to one's conjectural accuracy and the level of accuracy of one's truthfulness in conveying knowledge and that of data presented by others, and subsequent mental self-talk, prior to any outwardly observable physiological response to it. Digital analysis of the electrical properties of human brainwave activity (cycle-per-second waveforms) provides greater specificity as to the functional correlates of the brain's pre-cognitive, cognitive, somatosensory, and higher order mental function (i.e., the electrophysiological substrate of one's flow of consciousness).

The pre-conscious, pre-cognitive, brain state is different from the conscious, self-aware cognitive state. Pre-cognitive brainwave activation changes that enable a resultant cognitive state are analyzable and identifiable prior to one's conscious awareness of their impact on one's flow of consciousness and cognitive state. As experimentally demonstrated and described by Libet, pre-cognitive changes may take up to one-and-a-half seconds to manifest without any awareness of such changes taking place by the indwelling consciousness of the individual (B. Libet, "Cerebral Processes that Distinguish Conscious Experience from Unconscious Mental Function." In *The Principles of Design and Operation of the Brain*, John C. Eccles and Otto Creutzfeldt, Eds., Pontificiae Academiae Scientiarum Scripta Varia 78, Oct. 19-24, 1988, pp. 185-202).

Libet replicated the results of Deecke, Grozinger and Kornhuber, who quantified and isolated Electroencephalographic ("EEG") brainwave changes enabling what was to be a spontaneous act of individual volition, i.e., flexing a finger (L. Deecke, B. Grozinger, H. H. Kornhuber, "Voluntary Finger Movements in Man: Cerebral Potentials and Theory." Biological Cybernetics, 1976, 23, pp. 99-119). While the people in these studies consciously thought that they were instantly and spontaneously flexing their finger, their brains were observed to be building up the electrical potentials (pre-cognitively) that led to the finger flex for a time period ranging from one (1) second to one-and-a-half (1.5) seconds prior to the avowed spontaneous conscious execution of the finger flex.

When monitoring, analyzing, and utilizing biologic data (e.g., brainwave data, EEG data, electromyographic ("EMG") data, electrocardiogram ("ECG") data, galvanic skin response ("GSR") data, thermal skin temperature change data, and heart rate variability data), there are three key transition points along the path whereby a stimulus presented to the central nervous system results in cognition and volitional action: EEG Stage 1—the pre-stimulus state of activation immediately prior to stimulus introduction; EEG Stage 2—the instant of stimulus presentation which produces an automatic cerebral cascade of related neural network activation; and EEG Stage 3—the elapsed time between the presentation of a stimulus and the subsequent behavioral response. In neuropsychology, EEG Stage 3 is considered to be an index of how fast the thinker can execute the mental operations needed by the task at hand.

Conventional EEG and Quantitative EEG ("qEEG") methods and apparatus reference EEG energy in wide bands. Wide band (e.g., Delta, Theta, Alpha, and Beta) EEG methodology calculates energy output as follows. Delta is the average of the energy observed in the 0.5 Hz to 1 Hz and each of the 1 Hz through 4 Hz (i.e., 1 Hz, 2 Hz, 3 Hz, and 4 Hz) brainwave bands. Theta is the average of the energy observed in the 4 Hz through 8 Hz brainwave bands. Alpha is the average of the energy observed in the 8 Hz through 12 Hz brainwave bands. Beta is the average of the energy observed in the 13 Hz through 25 Hz brainwave bands. The Delta, Theta, Alpha, and Beta readings are all utilized as independent, standalone measures of EEG activity.

Additionally, wide band activity called Sensorimotor Rhythm ("SMR") is the average of the energy observed in each of the 12 Hz through 15 Hz brainwave bands, and it is also used as an independent stand alone measure of EEG activity. It is known to monitor EEG in terms of the sensed amplitudes and percentages of alpha, theta, beta, delta, and SMR brainwave activity.

BRIEF SUMMARY OF THE INVENTION

Briefly stated, in one aspect of the present invention, a method for creating a truth or lie scale for the purpose of detecting truth is provided, wherein a subject is fitted with equipment to monitor biologic data. The subject is presented with a stimulus which is designed to evoke an action to be performed by the subject, and that action is recorded. Biologic data is recorded before the stimulus is presented to the subject, and after presentation of the stimulus, and the change in biologic data is recorded. Further change in biologic data from the presentation of the stimulus to the completion of the action is recorded. Presentation of stimuli to the subject, and recording of the subject's actions in response to the stimuli continues for a pre-determined quantity of stimuli. The change in biologic data recorded before the presentation of the stimuli to after the action is taken by the subject is analyzed, and a truth or lie scale is created.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "an electrode" may include a plurality of electrodes. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Embodiments of the present invention generally relate to systems and methods for detecting truth utilizing biologic data. More specifically, the present invention relates to systems and methods for detecting truth utilizing biologic data observed during various time periods, or epochs, occurring prior and subsequent to the presentation of a stimulus to a subject and/or prior and subsequent to a volitional action performed by the subject in response to the stimulus. The biologic data collected during these various epochs is analyzed and manipulated in order to create a truth and/or lie scale for the particular subject. The truth and/or lie scales may then be used to detect the truthfulness of the actions (e.g., answering a question, agreeing to a statement, etc.) performed by the subject associated with the scale(s), wherein the actions are performed in response to a new stimulus (e.g., a statement, a question, etc.).

In one embodiment of the present invention, biologic data is monitored, recorded, analyzed, and/or utilized in three key transition points along the neurochromometric path during a session in which a stimulus is presented to a subject, wherein the stimulus prompts the subject to perform a volitional action. The presentation of the stimulus to the central nervous system of the subject results in cognition and volitional action on the part of the subject. The three key transition points are: 1) the pre-stimulus state of activation immediately prior to stimulus introduction (i.e., EEG Stage 1); 2) the instant of stimulus presentation producing an automatic cerebral cascade of related neural net activation (i.e., EEG Stage 2); and 3) the elapsed time between the presentation of a stimulus and the subsequent behavioral response (i.e., EEG Stage 3). In neuropsychology, EEG Stage 3 is considered to be an index of how fast the thinker can execute the mental operations needed by the task at hand. However, alternate embodiments of the present invention are envisioned in which biologic data observed at any one of these points, or alternate points, along the neurochromometric path may be added, deleted, or substituted without departing from the scope hereof.

Biologic data may be monitored in a variety of ways. In one embodiment of the present, an active electrode is mounted along the midline of the skull of the subject, and reference and ground electrodes are placed on opposite ears of the subject. EEG signals of the subject are detected by the depicted electrode array. However, alternate electrode placement sites may be substituted without departing from the scope of the present invention including, without limitation, any of the electrode placement sites identified in the internationally recognized 10-20 or Modified Combinatorial Nomenclature ("MCN") systems of electrode placement sites. Also, multiple electrode sites may be monitored in lieu of a single site without departing from the scope hereof.

Also, biologic data other than brainwave data may be monitored concurrently with the EEG data via use of additional sensor placements compatible with the type of biologic data to be monitored. Such biologic data may include, but is not limited to, EMG data, ECG data, GSR data, thermal skin temperature change data, and heart rate variability data. Equipment suitable for such measurements is manufactured by companies such as BioRadio. This biologic data may provide additional indication of the physical state of the subject in his or her truth-telling and lie-telling states. This information may be separately graphed or overlaid on the truth and lie detection scales such as those shown in FIGS. 5 and 6. However, such non-brainwave biologic data is not required to implement the present invention.

Figure 1:
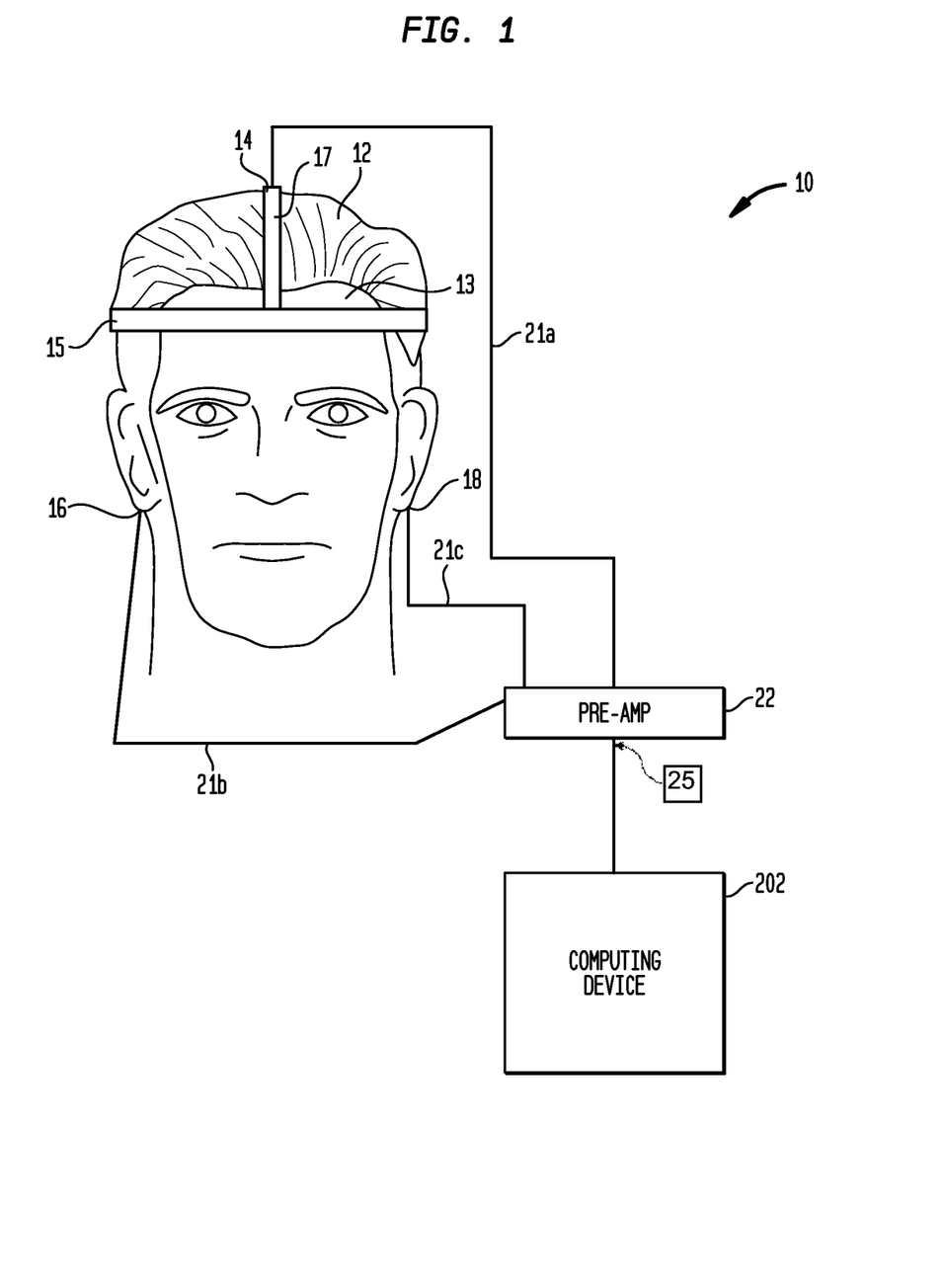
FIG. 1 is schematic diagram of a system for monitoring, recording, and/or analyzing biologic data in accordance with one embodiment of the present invention.

More specifically, referring now to FIG. 1, depicted is a schematic diagram of an exemplary system 10 for monitoring and/or analyzing biologic data in accordance with one embodiment of the present invention. In the depicted embodiment, a subject 12 is monitored with three electrodes 14, 16, and 18. Active electrode 14 is mounted as comfortably as possible along the midline of the skull of subject 12 to overlay the cerebral longitudinal fissure of subject 12. To accommodate this placement, an elasticized headband 15 is placed around the head parallel to the eyebrows and across the middle of the forehead 13 of subject 12. A second elasticized band 17 is placed across the top of the head of subject 12 and attaches to first band 15. Reference electrode 16 is placed on one ear of subject 12, and ground electrode 18 is placed on the other ear of subject 12. In the depicted embodiment, reference and ground electrodes 16 and 18, respectively, are attached with ear clips. However, alternate methods of attachment for electrodes 14, 16, and 18 may be substituted without departing from the scope hereof. It will also be appreciated by those skilled in the art that various sizes, shapes, quantities, and configurations of electrodes 14, 16, and 18 may be substituted without departing from the scope of the present invention. For example, in one alternative embodiment, active, reference, and ground electrodes 14, 16, and 18, respectively, may be incorporated into a skullcap to facilitate the monitoring of brainwaves at any one, any combination of two or more, or the whole array of electrode placement sites defined in the 10-20 or MCN system(s) of electrode sites. Also, headbands, headsets, or other devices may be utilized to facilitate monitoring of a plurality of such electrode sites without departing from the scope thereof.

In the depicted embodiment, the signals detected by the electrode system comprised of electrodes 14, 16, and 18 are conveyed by electrode connectors 21a, 21b, 21c to preamplifier 22. However, alternate methods of transmitting these signals may be substituted without departing from the scope hereof including, without limitation, wireless transmission (e.g., Radio Frequency ("RF"), infrared, etc.). Wireless transmission will allow the subject to have a wider range of movement during the monitoring/recording session. In such an embodiment, a remote transmitter may be attached to, for example, first headband 15. The wireless signals may be received by a compatible receiver integral to, or external to, computing device 202.

Preamplifier 22 amplifies and optically isolates the detected bioelectric and EEG brainwave signals received via connectors 21a, 21b, 21c. Preferably preamplifier 22 amplifies these signals by a factor ranging from approximately ten (10) to approximately one hundred (100). In the depicted embodiment, preamplifier 22 is manufactured by Biofeedback Systems as Medical Pre-Amplifier Model PA-2M. However, alternate preamplifiers may be substituted without departing from the scope hereof. Also, although in the depicted embodiment of the present invention, preamplifier 22 is a separate component from computing device 202, it will be appreciated by those skilled in the art that a preamplifier capability may be built into computing device 202 rather than using a separate preamplifier 22.

In the depicted embodiment, the bioelectric signals are monitored in a frequency range ranging from approximately zero (0) to approximately one hundred and sixty (160) Hz with bandwidth resolutions of approximately one (1) hertz or less around each frequency in the range. However, alternate embodiments are envisioned in which varying frequency ranges and/or varying bandwidth resolutions are substituted without departing from the scope hereof.

In the depicted embodiment, preamplifier 22 amplifies and optically isolates the detected bioelectric and EEG brainwave signals. The amplified data is transmitted to a signal processor such as computing device 202 as described in greater detail herein. The amplified signals are transmitted to computing device 202 via connection 25 such that they may be read or otherwise interpreted by processing unit 218 of computing device 202. Connection 25 may be any connection capable of transferring signals including, without limitation, wireless connections, USB connections, and the like.

Figure 2:
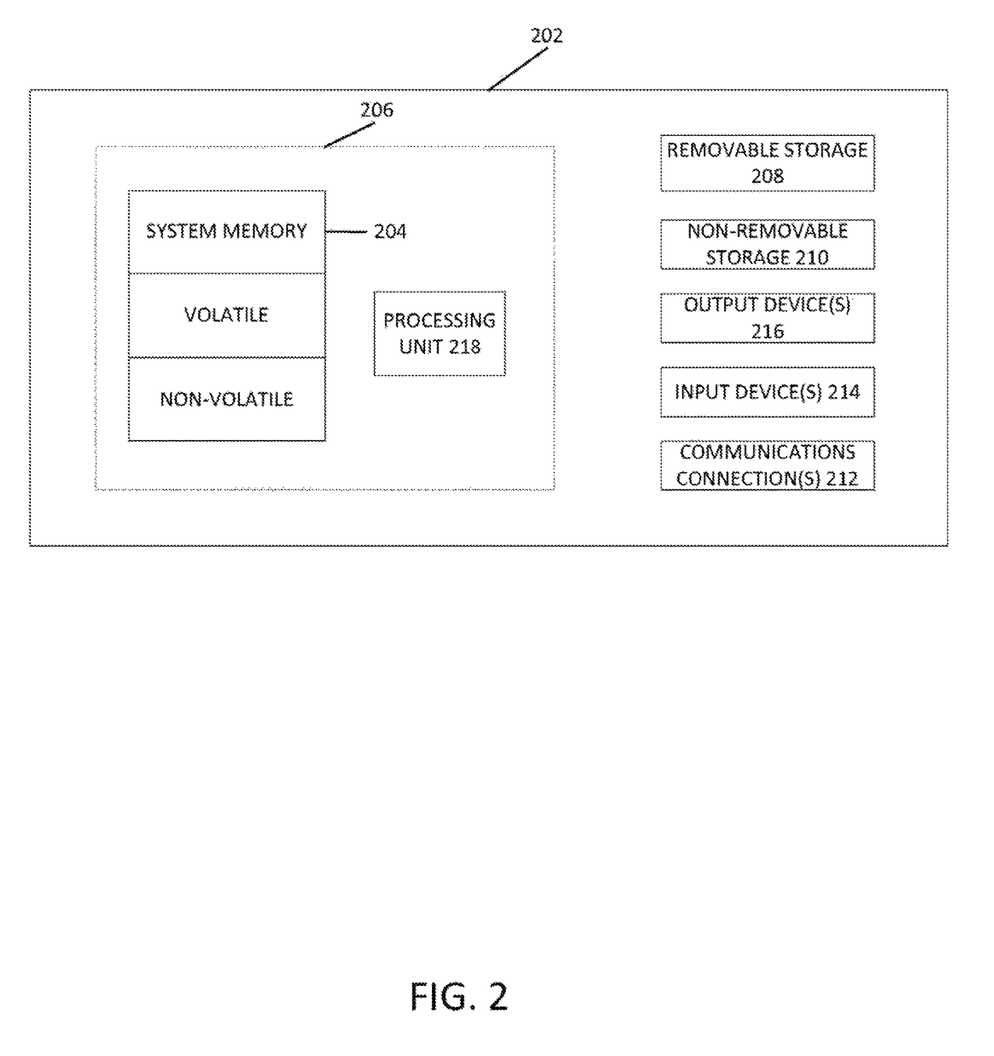
FIG. 2 depicts a block diagram of an exemplary computing device for use with the system depicted in FIG. 1.

Turning now to FIG. 2, depicted is an exemplary computing device 202 for use with system 10 as described above. The depicted computing device is only one example of a suitable computing device and is not intended to suggest any limitation as to the scope of use or functionality. Numerous other general purpose or special purpose computing system devices, environments, or configurations may be used. Examples of well-known computing systems, environments, and/or configurations that may be suitable for use include, but are not limited to, personal computers ("PCs"), server computers, handheld or laptop devices, multi-processor systems, microprocessor-based systems, network PCs, minicomputers, mainframe computers, cell phones, tablets, embedded systems, distributed computing environments that include any of the above systems or devices, and the like.

Computer-executable instructions such as program modules executed by a computer may be used. Generally, program modules include routines, programs, objects, components, data structures, etc. which perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

In the depicted embodiment, computing device 202 includes at least one processing unit 218 and at least one memory 204. Depending on the exact configuration and type of the computing device, memory 204 may be volatile (such as random access memory ("RAM")), non-volatile (such as read-only memory ("ROM"), flash memory, etc.), or some combination of the two. This most basic configuration is illustrated in FIG. 2 by lines 206. In addition to that described herein, computing devices 202 can be any web-enabled handheld device (e.g., cell phone, smart phone, or the like) or personal computer including those operating via Android™, Apple®, and/or Windows® mobile or non-mobile operating systems.

Figure 3:
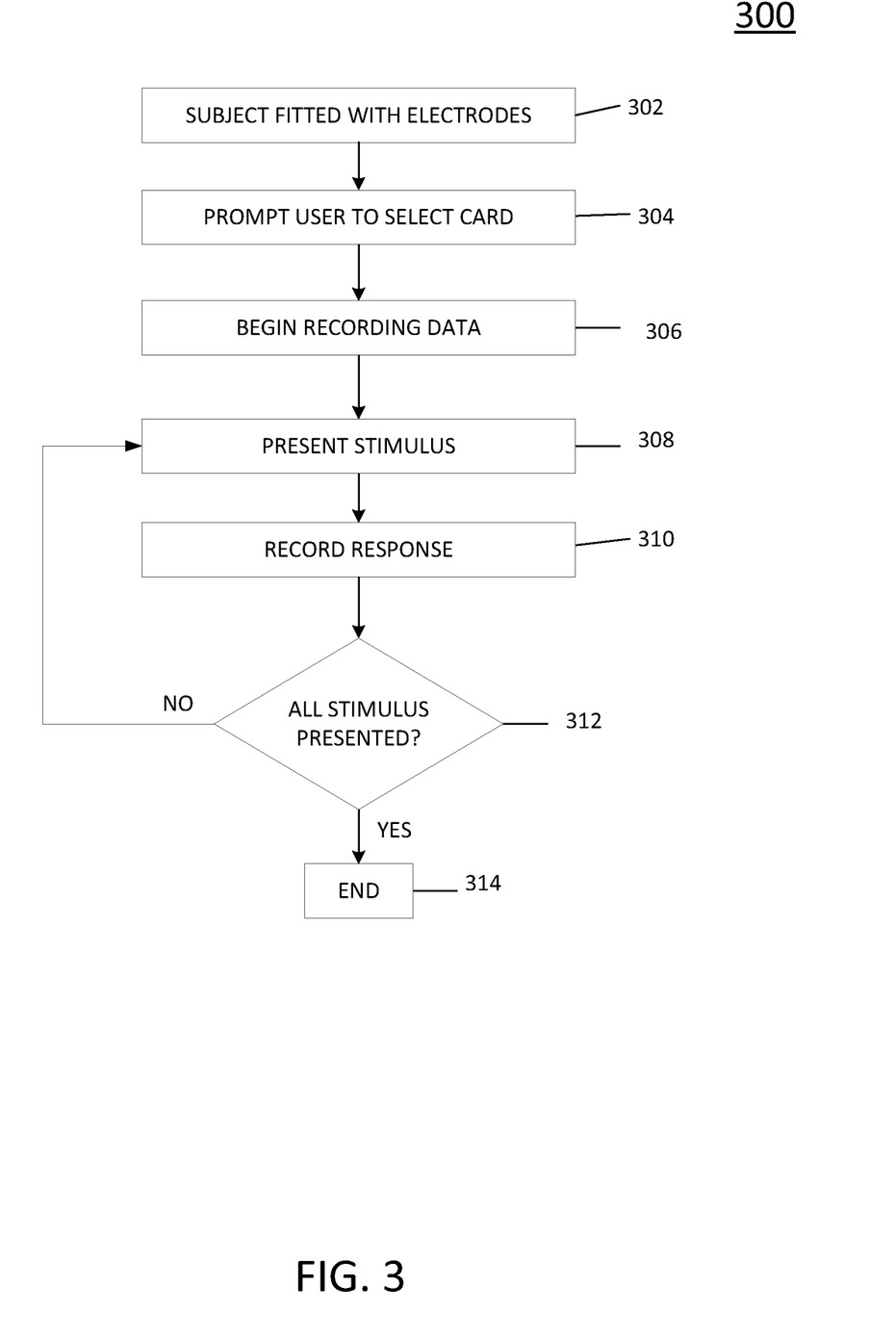
FIG. 3 depicts an exemplary flowcharts for a computer program for obtaining and recording the necessary data for creation of a truth and/or lie scale in accordance with one embodiment of the present invention.

Computing device 202 may have additional features/functionality. For example, computing device 202 may include additional storage (removable and/or non-removable) including, but not limited to, magnetic or optical disks or tape, thumb drives, and external hard drives as applicable. Such additional storage is illustrated in FIG. 3 by removable storage 208 and non-removable storage 210.

Computing device 202 typically includes or is provided with a variety of computer-readable media. Computer-readable media can be any available media that can be accessed by computing device 202 and includes both volatile and non-volatile media, removable and non-removable media. By way of example, and not limitation, computer-readable media may comprise computer storage media and communication media.

Computer storage media includes volatile and non-volatile, removable and non-removable media implemented in any method or technology for storage of information such as computer-readable instructions, data structures, program modules or other data. Memory 204, removable storage 208, and non-removable storage 210 are all examples of computer storage media. Computer storage media includes, but is not limited to, RAM, ROM, electrically erasable programmable read-only memory ("EEPROM"), flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can accessed by computing device 202. Any such computer storage media may be part of computing device 202 as applicable.

Computing device 202 may also contain communications connection 212 that allows the device to communicate with other devices including, without limitation, preamplifier 22. Such communications connection 212 is an example of communication media. Communication media typically embodies computer-readable instructions, data structures, program modules and/or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency ("RF"), infrared and other wireless media. The term computer-readable media as used herein includes both storage media and communication media.

Computing device 202 may also have input device(s) 214 such as keyboard, mouse, pen, voice input device, touch input device, etc. Output device(s) 216 such as a display, speakers, printer, etc. may also be included. All these devices are generally known to the relevant public and therefore need not be discussed in any detail herein except as provided.

It should be understood that the various techniques described herein may be implemented in connection with hardware or software or, as appropriate, with a combination of both. Thus, the methods and apparatus of the presently disclosed subject matter, or certain aspects or portions thereof, may take the form of program code (i.e., instructions, scripts, and the like) embodied in tangible media, such as floppy diskettes, CD-ROMs, hard drives, flash drives, DVDs or any other machine-readable storage medium wherein, when the program code is loaded into and executed by a machine, such as a computer, the machine becomes an apparatus for practicing the presently disclosed subject matter.

Although exemplary embodiments may refer to utilizing aspects of the presently disclosed subject matter in the context of one or more stand-alone computer systems, the subject matter is not so limited, but rather may be implemented in connection with a multi-computer computing environment. Still further, aspects of the presently disclosed subject matter may be implemented in or across a plurality of processing chips or devices, and storage may similarly be affected across a plurality of computing devices 202. Such devices might include personal computers, network servers, and handheld devices (e.g., cell phones, tablets, smartphones, etc.), for example.

Turning back to FIG. 1, once the amplified signals are received by computing device 202, a fast fourier transform ("FFT") and/or other bioelectric signal analyses are performed on the collected bioelectric and EEG brainwave signal data. These analyses may be performed via software within the computing device 202 and displayed as desired on the computer screen or stored within the computer or other external data storage device. As discussed above, in the depicted embodiment, the collected bioelectric and EEG brainwave signal data will be in the range of approximately 0 to 160 Hz with a bandwidth resolution of one hertz or less around a given frequency. Raw bioelectric and EEG brainwave signal data and/or its subsequent analysis may be stored in a memory such as memory 204 of computing device 202 or by other means without departing from the scope hereof. However, alternate frequency ranges and/or bandwidth resolutions may be substituted without departing from the scope hereof.

More specifically, computing device 202 performs a FFT on the amplified bioelectric signal to determine the amplitude of the bioelectric signal. In the depicted embodiment, the amplitudes of the signals are measured in microvolts. Once these signals are processed, brainwave signatures may be created for the subject. The composite amplitude of the signal is determined by performing an FFT on the amplified signal. A frequency window of up to approximately one (1) Hz around a frequency defines a bioelectric frequency band. Sampling of the bioelectric signals by computing device 202 may be performed, for example, at a rate of about 8,000 samples per second.

EEG analysis software allows the user to monitor bioelectric bandwidths of interest from the detected bioelectric signals. A window of 1 hertz or less is the bioelectric bandwidth of interest. Computing device 202 executes EEG analysis software to display particular bandwidths of interest on a computing device output device(s) 216 such as a monitor or the like. In the depicted embodiment, the data is refreshed on the output device(s) 216 in one second intervals and the monitoring and processing of the bioelectric signals is ongoing. In the depicted embodiment, EEG analysis software is manufactured by In Sync Institute Inc., as EEG Brainwave Analysis Program, however, alternate software may be substituted without departing from the scope of the present invention. This allows digital readings for each monitored bandwidth's varying peak-to-peak microvolt value to be displayed on output device(s) 216.

For example, if the user chooses to monitor a bioelectric bandwidth of 14 hertz, the window will be from about 13.5 hertz to about 14.5 hertz. The amplitude values of the bioelectric signals related to the bandwidths of interest can be displayed in a first window of a computer display. Also, an average value of the amplitude of the bioelectric signal over time can be displayed in a second window of the computer display. The amplitude values of the bioelectric signals of the bandwidths of interest collected throughout the entire session are stored in the memory such as memory 204 of the computer such as computing device 202 to allow a monitoring session to be replayed and/or re-analyzed. Also, detected amplitudes for all bandwidths in the 0 to one hundred sixty (160) hertz range can be stored in the memory such as memory 204 of computing device 202.

In the depicted embodiment of the present invention, the data received from electrode connectors 21a, 21b, 21c by preamplifier 22 is measured and recorded to create truth detection scales such as a truth scale and a lie scale for the subject 12. The biologic data collected and recorded as described above is further evaluated to compare and contrast the signals obtained during EEG Stages 1, 2, and 3 and the changes thereto between these stages. This allows the unconscious and/or pre-cognitive state to be differentiated from the conscious and/or cognitive state of a person's central nervous system when it is responding to a stimulus or other outside influence.

Referring now to FIG. 3, depicted is an exemplary computer program for obtaining the necessary data for creation of a truth detection scale in accordance with the depicted embodiment.

Process 300 starts at 302, at which the subject 12 is fitted with a plurality of electrodes 14, 16, and 18, for example, in the manner discussed above and is seated in front of computing device 202. One set of stimuli includes a plurality of traditional playing cards having values ranging from one through ten. However, varying stimuli, or sets of stimuli, tailored to specific venues of questioning such as visual, auditory, or other sensory questioning may be substituted without departing from the scope hereof.

In the depicted embodiment, the stimuli are arranged face down on a table or other surface on which computing device 202 is resting such that they are between the user and the computing device 202. In the depicted embodiment, ten playing cards are used; however, alternate quantities may be substituted without departing from the scope of the present invention. Once the subject is fitted and seated in front of computing device 202, the subject notifies computing device 202 by clicking a proceed button or the like via input device(s) 214 such as a mouse, touchpad, or the like. Process 300 then proceeds to 302.

At 304, the subject is prompted to select a card by turning the card over via a visual direction displayed to the subject via an output device(s) 216 such as a display device. That is, the subject 12 is provided with a choice and the subject makes a volitional action in response to the choice. Once the subject turns over the desired card such that it is face up and its value can be seen, the subject notifies computing device 202 by clicking a proceed button or the like and process 300 proceeds to 306. For explanation purposes, we will use an example in which the subject turned over a card having a value of five (5).

At 306, process 300 begins recording all data received from preamplifier 22 via execution of EEG analysis software or the like as discussed in greater detail above. Raw data may also be separately recorded or recorded via such software. In the depicted embodiment, the data will continue to be recorded from step 306 until the conclusion of process 300. The data is continuously saved in a memory such as memory 204 for current and future analysis. However, alternate embodiments are envisioned in which recording and/or storing is not a continuous process.

Next, at 308, process 300 presents a stimulus to subject 12. In the depicted embodiment, the first stimulus is the statement "The card that you chose and turned over is an Ace". At 310, the subject's response is recorded. This response may be entered by the subject by his or her clicking of a "Yes" or "No" button or the like. In the depicted embodiment, the subject has turned over one card only, for example, a card having a value of five. Prior to the execution of process 300, the subject is directed to answer yes, or to agree with, all of the statements for each card value. Therefore, the subject is not being truthful when agreeing with all statements other than "The card that you chose and turned over is a Five." In this manner, process 300 is able to record the brainwave activity that occurs when the subject is not telling the truth.

Next, at 312, process 300 determines whether all stimuli have been presented to the user. In the depicted embodiment, the subject is asked if he or she turned over an Ace, Two, Three, Four, Five, Six, Seven, Eight, Nine, and Ten (i.e., ten different stimuli are presented to subject 12). If not all stimuli have been presented, process 300 returns to 308 at which the next stimulus is presented to subject 12. If all of the stimuli have been presented (e.g., all ten statements have been presented and the respective answers recorded), process 300 proceeds to 314, at which it ends and recording of the data received from preamplifier 22 ends. As discussed in greater detail above, from step 306 to step 314, process 300 continuously records the data received from preamplifier 22 for each frequency ranging from approximately 0 Hz (i.e., the start frequency) to approximately one hundred sixty (160) Hz (i.e., the end frequency). The data is recorded in toto in real-time from step 306 through the end of process 300 to allow it to be re-analyzed and/or otherwise used at a future date. Although the depicted embodiment of the present invention utilized ten stimuli, alternate quantities may be substituted without departing from the scope hereof.

Figure 4:
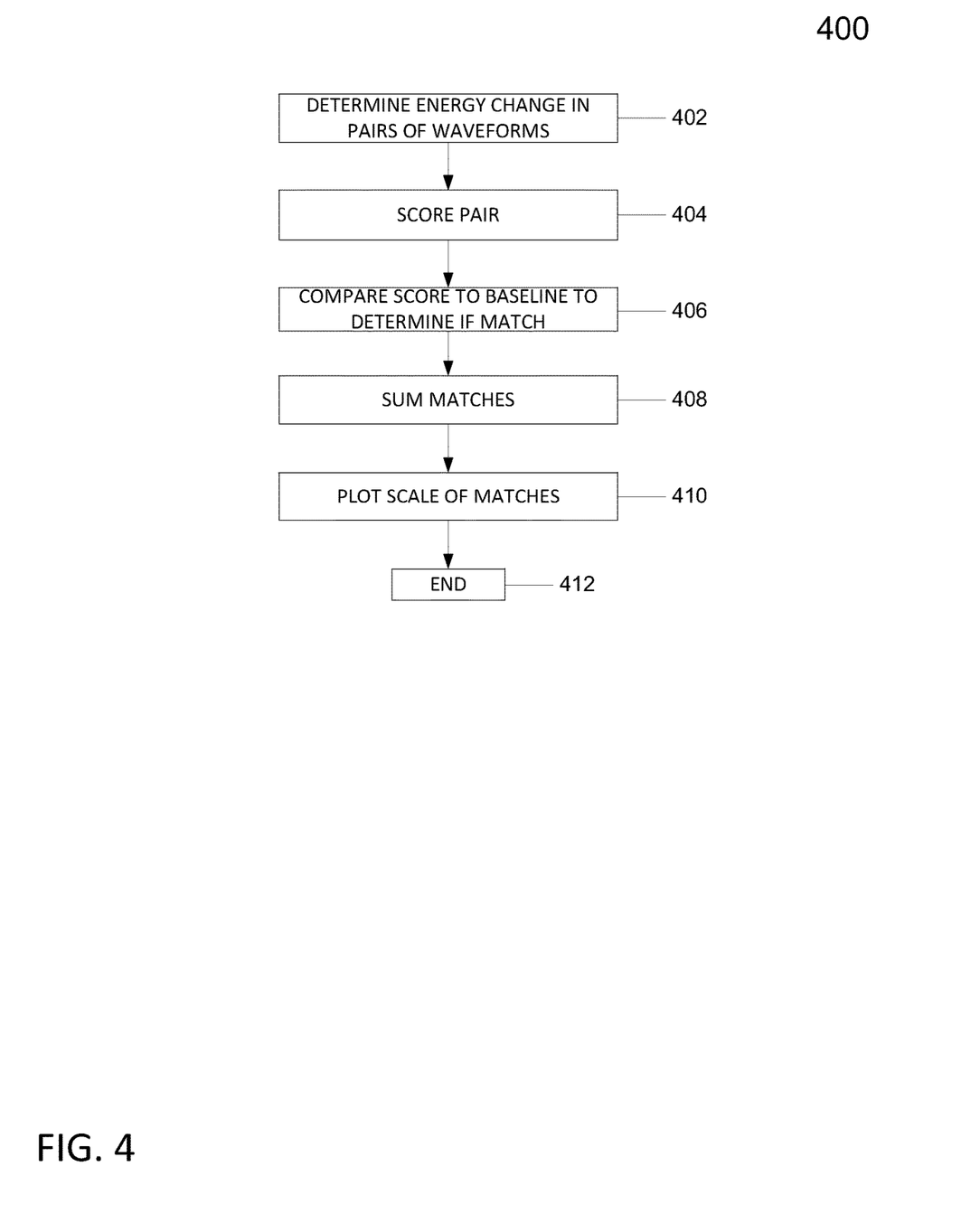
FIG. 4 depicts an exemplary flowchart for a computer program for creating truth or lie scales in accordance with one embodiment of the present invention.

After data for a particular subject 12 has been recorded, truth detection scales may be generated from such data utilizing a process such as process 400 as depicted in FIG. 4. Turning now to FIG. 4, depicted is a flowchart of an exemplary process for generating truth detection scales in accordance with one embodiment of the present invention. Process 400 begins at 402, at which the energy change of each waveform in a pair of waveforms is determined.

In the depicted embodiment, the energy change being measured at step 402 is the change in energy from a second epoch to a third epoch, wherein the second epoch occurs subsequent to presentation of a stimulus and the third epoch occurs subsequent to an action performed by the subject. In the depicted embodiment, the second and third epochs each have a duration of approximately one second. In this manner, the energy change during the waveforms produced in EEG Stage 3 (i.e., the elapsed time between the presentation of a stimulus and the subsequent behavioral response) are monitored. More specifically, in the depicted embodiment, the change in waveform energy is analyzed during the time period that encompasses the action of entering "true" or "false" in response to a stimulus such as that presented at step 308 of process 300. However, alternate epoch timing and/or epoch durations may be substituted without departing from the scope hereof. Separate, concurrent analyses for change directionality are computed as additional measures confirming the brain/mental state under consideration. The same spreadsheet or other algorithmic tool may be used, however, the directionality of the data may change. For example, in the depicted embodiment, the directionality of the change in amplitude of any brainwave configuration is monitored and/or recorded including, without limitation: 1) no change in the amplitude of a single one (1) Hz brainwave; 2) a decrease in the amplitude of a single one (1) Hz brainwave; 3) both amplitudes of a selected pair of brainwaves increase; 4) both amplitudes of a selected pair of brainwaves decrease; and/or 5) the amplitudes of a selected pair of brainwaves differ (i.e., one increases and the other decreases). These analyses are merely exemplary and various combinations of brainwaves and/or single brainwaves may be analyzed in a variety of manners without departing from the scope thereof.

In the depicted embodiment, the energy change between a second epoch and a third epoch for a plurality of waveform pairs is analyzed. Data collected or calculated during this time period may be referred to herein as second change data. In the exemplary embodiment shown in FIGS. 1 through 6, a pair set is created for each frequency in the range of frequencies (e.g., 2 Hz through 160 Hz). Each pair set includes a pair for each frequency value in the frequency range other than the frequency value for which the pair set is being created. Each pair includes first pair data and second pair data. The first pair data is second change data for the frequency for which the pair set is being created. The second pair data is second change data for the other frequency associated with the pair.

For example, the pairs are created as follows: the value of each frequency in the monitored range with the exception of 0 and 1 Hz (e.g., 2 Hz through 160 Hz) is paired with all other frequencies in the range. For example, 2 Hz is paired with all frequencies in the range other than itself, 0 Hz, and 1 Hz (i.e., it is paired with 3 Hz through 160 Hz). A pair set may be created for a first frequency (e.g., 2 Hz) as follows. The 2 Hz pair set includes a pair for each frequency value in the frequency range other than the frequency value for which the pair set is being created (3 Hz through 160 Hz). Each pair in the pair set includes first pair data and second pair data. The first pair data is second change data for the frequency for which the pair set is being created (i.e., 2 Hz). The second pair data is second change data for the other frequency associated with the pair (3 Hz through 160 Hz).

That is, the pair set for a first frequency such as 2 Hz includes second change data for a first pair of frequencies 2 Hz and 3 Hz, second change data for a second pair of frequencies 2 Hz and 4 Hz, second change data for a third pair of frequencies 2 Hz and 5 Hz and so on through the final pair of frequencies 2 Hz and 160 Hz. And, similarly, the pair set for 3 Hz pairs second change data for 3 Hz with second change data for all frequencies in the range other than itself, 0 Hz, and 1 Hz (i.e., it is paired with 2 Hz, and 4 Hz through 160 Hz). That is, the pair set for a frequency such as 3 Hz includes second change data for a first pair of frequencies 3 Hz and 2 Hz, second change data for a second pair of frequencies 3 Hz and 4 Hz, second change data for a third pair of frequencies 3 Hz and 5 Hz and so on through the final pair of frequencies 3 Hz and 160 Hz. In this manner, pair sets are created for all frequencies in the range from 2 Hz to 160 Hz. However, alternate frequency ranges may be substituted without departing from the scope of the present invention. Also, alternate frequency pairs and/or pair sets may be substituted without departing from the scope hereof (e.g., all even pairs, all odd pairs, etc.). Once all of the energy change values have been determined for each waveform in all of the pairs of waveforms described above in step 402, process 400 proceeds to 404.

At 404, each pair of waveforms is scored with a pair score. If the energy value for each of both waveforms, of any given pair, change in the desired direction, the pair is given a positive pair score such as a 1. The possible directions for the pair of energy levels are: 1) both energy values change in the same direction; 2) both energy values change in opposite directions; 3) or no change occurs in at least one of the energy values. In the depicted embodiment of the present invention, the desired direction occurs when both energy values in the pair change in the same direction, regardless of the quantity of change. In this scenario, the pair is scored with a positive score value such as a one (1). If the change does not occur in this desired direction, the pair is scored with a negative pair score such as a zero (0). However, alternate embodiments are envisioned in which an analysis may be performed for different desired directions without departing from the scope hereof.

Next, at step 406, the pair scored in step 404 is compared to a baseline value to determine whether there is a match. In the depicted embodiment, each frequency in the range of frequencies has one (1) baseline value for each stimulus presented to the subject such as, for example, during step 308 of process 300. The baseline value is a one (1) or a zero (0) and is created in a manner similar to the scoring of the pairs, however, the baseline value is created based upon brainwave activity measured between the first and second epochs.

More specifically, in the depicted embodiment, the energy change utilized to create the baseline for each frequency is the change in energy from a first epoch to a second epoch, wherein the first epoch occurs during presentation of a stimulus (i.e., the pre-conscious sensory detection phase) and the second epoch occurs subsequent to presentation of a stimulus (i.e., the perception/comprehension phase) (the same second epoch as described above with respect to step 402). Data collected or calculated during this time period may be referred to herein as first change data. In the depicted embodiment, the first and second epochs each have a duration of approximately one (1) second. In this manner, the energy change during the waveforms produced in EEG Stage 2 (i.e., the instant of stimulus presentation which produces an automatic cerebral cascade of related neural network activation)) is utilized to create a baseline value. More specifically, in the depicted embodiment, the change in waveform energy is analyzed during the time period that encompasses the presentation of the stimulus (such as the statement presented at step 308 of process 300) to the subject and the subject's cognition of the stimulus (e.g., statement). However, alternate epoch timing and/or epoch durations may be substituted for creation of a baseline without departing from the scope hereof.

These changes in energy levels for each of the baseline pairs of waveforms (i.e., the same pairs discussed above with respect to step 402 except that the data is recorded between the first and second epochs instead of the second and third epochs) are scored with a baseline pair score in a similar manner as discussed above.

More specifically, each pair of baseline waveforms is scored with a baseline pair score. If the energy value for each of both waveforms, of any given baseline pair, change in the desired direction, the baseline pair is given a positive baseline pair score such as a 1. The possible directions for the baseline pair of energy levels are: 1) both energy values change in the same direction; 2) both energy values change in opposite directions; 3) or no change occurs in at least one of the energy values. In the depicted embodiment of the present invention, the desired direction occurs when both energy values in the baseline pair change in the same direction, regardless of the quantity of change. In this scenario, the baseline pair is scored as a positive baseline score such as a one (1). If the change does not occur in this desired direction, the baseline pair is scored with a negative pair score such as a zero (0). However, alternate embodiments are envisioned in which an analysis may be performed for different desired directions without departing from the scope hereof.

For each frequency and/or each stimulus, a first baseline value is assigned to a frequency of said frequency range and/or a stimulus for which a quantity of positive baseline pair scores is equal to or exceeds a predetermine percentage. For example, if sixty percent (60%) or more of the scored baseline pairs associated with the specific frequency and stimulus have been scored with a one, then the baseline value is set to a first baseline value (e.g., a one). Otherwise, the baseline value is set to a second baseline value (e.g., zero). However, alternate predetermined percentages other than sixty percent (60%) may be substituted without departing from the scope hereof. Also, a cutoff value may be used in lieu of a predetermined percentage without departing from the scope hereof.

Therefore, for example, the baseline value for a frequency of 2 Hz for a stimulus in which the subject agreed with the statement "The card that you chose and turned over is an Ace" is determined by scoring the baseline energy change for all 2 Hz frequency pairs in the baseline pair set associated with that frequency and/or stimulus (i.e., 2 Hz and 3 Hz, 2 Hz and 4 Hz, 2 Hz and 5 Hz and so on through 2 Hz and 160 Hz). If sixty (60) percent or more of these 2 HZ pairs have a positive baseline pair score of, for example, one, then the baseline value for that stimulus and 2 Hz is set to a first baseline value (e.g., one). If less than sixty (60) percent of these pairs have a positive baseline pair score of, for example, one, then the baseline value for that stimulus and 2 Hz is set to a second baseline value (e.g., zero).

At step 408, each pair scored at step 406 in the pair set for a particular frequency and/or a particular stimulus is compared to the baseline value associated with the particular frequency and/or stimulus to determine if there is a match between the pair's score and the baseline value. Each pair that has a score that matches the baseline value is assigned a match value (e.g., one) and each pair that has a score that does not match the baseline value is assigned a non-match value (e.g., zero). The match values are then summed for the specific frequency and/or stimulus. This process is performed for each frequency per stimulus. Process 400 then proceeds to 410.

At 410, the quantity of matches for each stimulus is summed to create a total match value. For example, for the stimulus in which the subject was asked if he or she turned over an ace, the quantity of matches for 2 Hz is summed with the quantity of matches for 3 Hz, 4 Hz, and 5 Hz through 76 Hz. The same summing process is performed for each of the stimuli presented to the subject such as, for example, at step 308 of process 300. These sums may be utilized to create a truth scale as discussed with respect to step 412.

Figure 6:
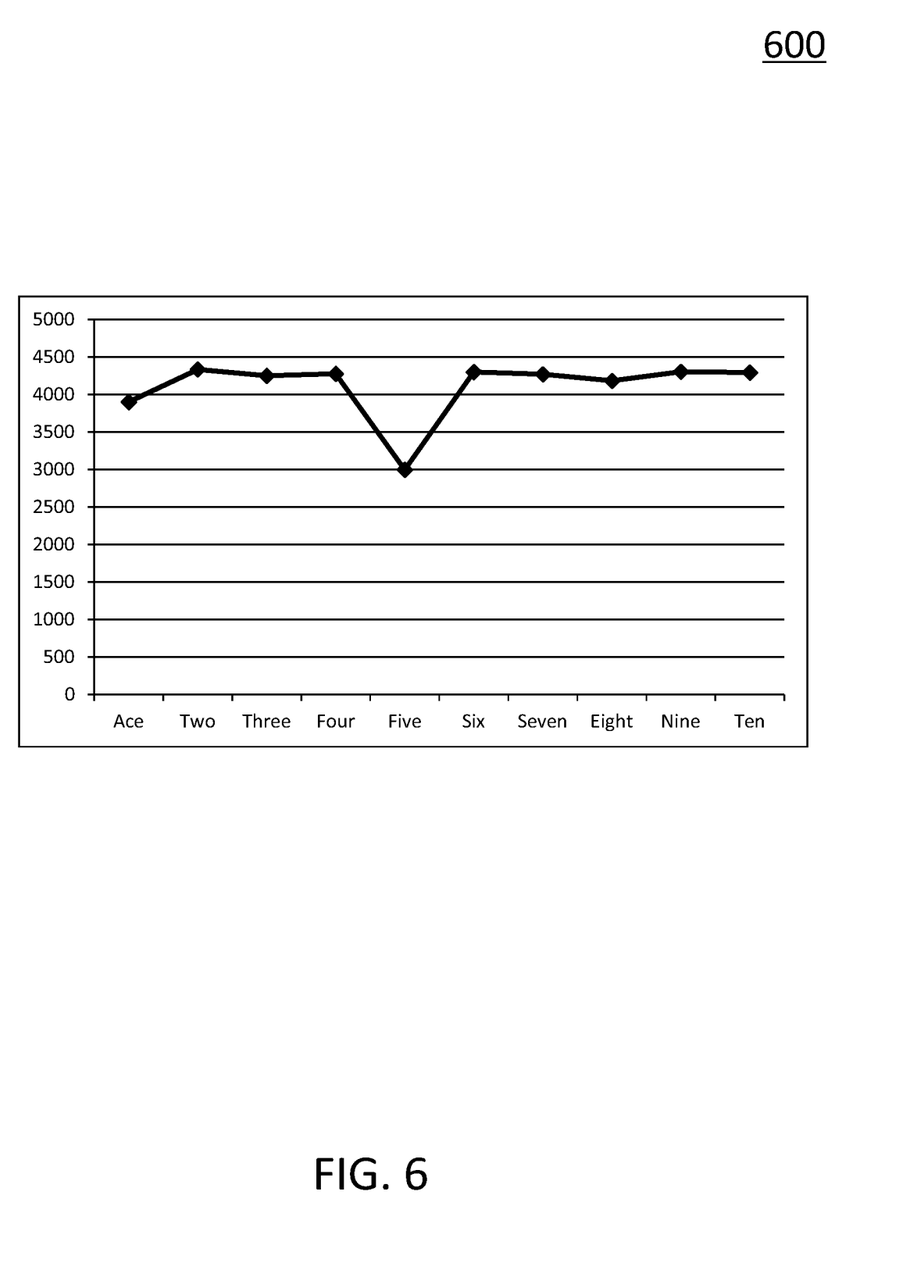
FIG. 6 depicts an exemplary lie scale created in accordance with one embodiment of the present invention.

Alternatively, rather than assigning a value of, for example, one to matches, this value may be assigned to non-matches as a non-match value. In this scenario, the quantity of non-match values for each stimulus may also be summed. For example, for the stimulus in which the subject was asked if he or she turned over an ace, the quantity of non-matches for 2 Hz is summed with the quantity of non-matches for 3 Hz, 4 Hz, and 5 Hz through 76 Hz. These values may be utilized to create a lie scale as depicted in FIG. 6.

Figure 5:
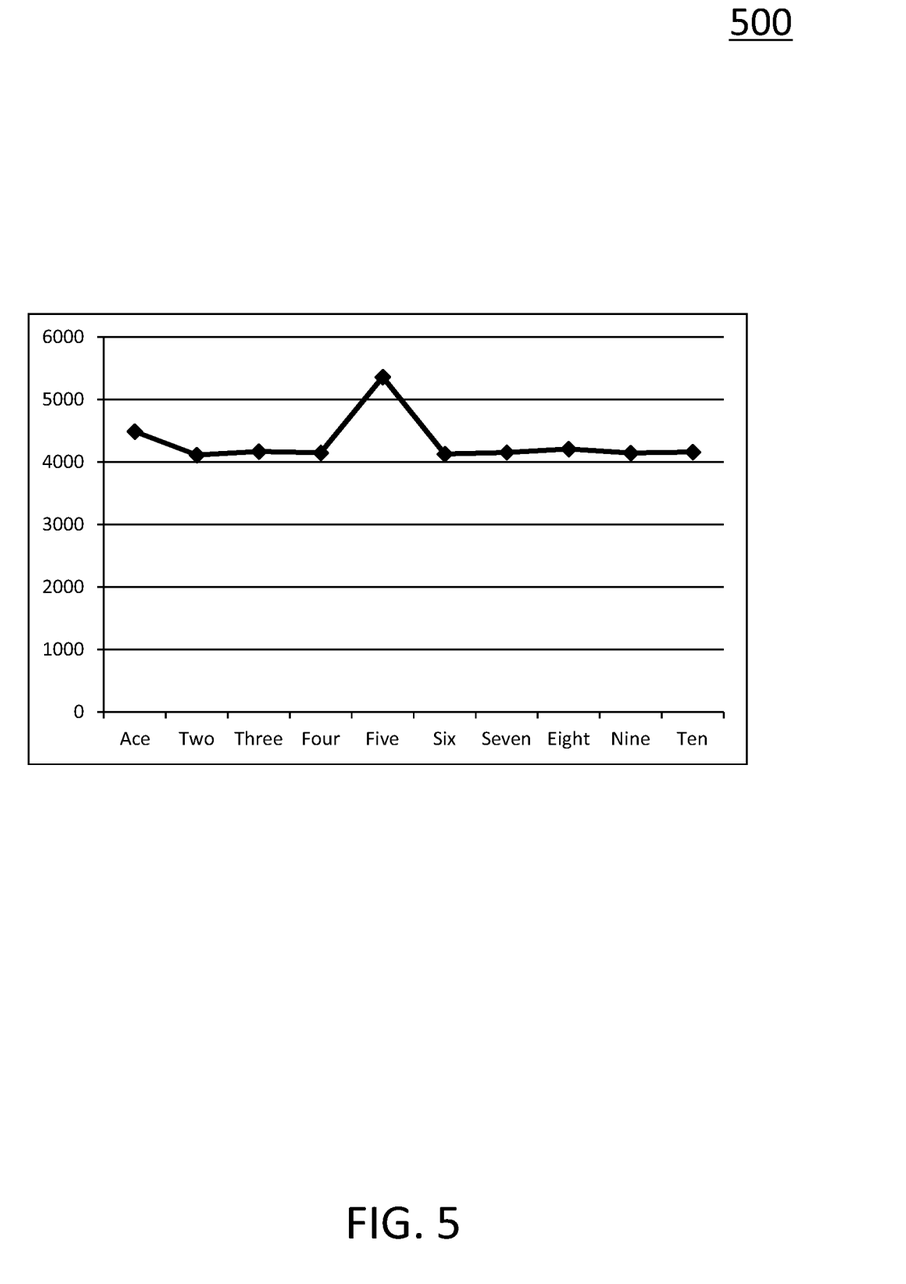
FIG. 5 depicts an exemplary truth scale created in accordance with one embodiment of the present invention.

Next, at step 412, the total match values determined at step 410 are plotted to create a truth scale. One such exemplary truth scale 500 is depicted in FIG. 5. The stimuli are plotted on the y axis and the quantity of matches associated with each stimuli is plotted on the x axis. As can be seen in the exemplary scale shown in FIG. 5, the total match quantity for the one stimulus in which the subject was truthfully in agreement with the statement is significantly higher than the quantity of matches for the stimuli for which a false agreement was provided. In the depicted embodiment, the difference is approximately one thousand, however, alternate values may be determined when performing the processes described herein without departing from the scope of the present invention.

Alternatively, at step 412, the sums of non-matches determined at step 410 may be plotted to create a lie scale. One such exemplary lie scale 600 is depicted in FIG. 6. The stimuli are plotted on the y axis and the quantity of non-matches associated with each stimuli is plotted on the x axis. As can be seen in the exemplary scale shown in FIG. 6, the quantity of non-matches for the one stimulus in which the subject was truthfully in agreement with the statement is significantly lower than the quantity of non-matches for the stimuli for which false agreement was provided. In the depicted embodiment, the difference is slightly less than one thousand, however, alternate values may be determined when performing the processes described herein without departing from the scope of the present invention.

Once a truth or lie scale has been generated in accordance with the above processes, one or both of these scales may be used to determine whether a subject is being truthful when responding to a new stimulus (e.g., a statement or a question). The new stimulus is presented in the same manner as described above with respect to steps 306 through 314 of process 300 and the biologic data is recorded during the time period prior to, during, and subsequent to presentation of the stimulus and the subject providing an action in response thereto.

After the biologic data has been recorded, it may be analyzed in a manner such as that described above with respect to FIG. 4. When all of the matches have been summed such as described above with respect to step 408 of FIG. 4, the sum may be compared to the values on the truth or lie scale to determine in which range the sum falls. For example, if utilizing the truth scale depicted in FIG. 5, a sum equal to or greater than four thousand seven hundred fifty (4,750) may be deemed to be a truthful response and a sum less than four thousand seven hundred fifty may be deemed to be a non-truthful response. Or, if a lie scale is utilized such as that depicted in FIG. 6, a sum equal to or less than three thousand five hundred (3,500) may be deemed to be a truthful response and a sum greater than three thousand five hundred may be deemed to be a non-truthful response. However, other cut-off values may be utilized to determine truthfulness or non-truthfulness without departing from the scope of the present invention.

Although several processes have been disclosed herein as software, it may be appreciated by one of skill in the art that the same processes, functions, etc. may be performed via hardware or a combination of hardware and software. Similarly, although the present invention has been depicted as a hardwired system, these concepts may be applied to wireless systems and hybrid hardwired and wireless systems without departing from the scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for determining whether an action performed by a subject is true comprising the steps of:
   (i) fitting a subject with equipment to monitor Electroencephalographic data, the Electroencephalographic data including a plurality of frequencies in a frequency range, adjacent frequencies in said frequency range being separated by approximately one hertz;
   (ii) presenting a stimulus to said subject, said stimulus designed to evoke the action performed by said subject, the action including providing an answer to a question, said stimulus being any one of a plurality of different questions;
   (iii) recording said action;
   (iv) recording, via a computing device, a first change of each of the plurality of frequencies between a first epoch and a second epoch as first change data, said first epoch occurring during presentation of said stimulus, and said second epoch occurring subsequent to presentation of said stimulus;
   (v) recording, via said computing device, a second change of each of the plurality of frequencies between said second epoch and a third epoch as second change data, said third epoch occurring subsequent to said action;
   (vi) repeating steps (ii) through (v) until a predetermined quantity of said stimulus of any one of the plurality of different questions have been presented to said subject and the actions performed by said subject in response to said predetermined quantity of said stimulus of any one of the plurality of different questions have been recorded, wherein a truth of a first set of said actions is known prior to performing step (iii) of the method and a truth of a second set of said actions is unknown prior to performing step (iii) of the method;
   (vii) selecting an analysis frequency range;
   (viii) for each action in said first set of said actions, determining a baseline value for each frequency of said plurality of frequencies in the analysis frequency range, said baseline value determined from said first change data;
   (ix) for each of said action in said first set of said actions and said second set of said actions, creating a plurality of pair sets for each of said frequency of said plurality of frequencies in the analysis frequency range, each pair set of the plurality of pair sets includes a pair of first and second values, the first value of each pair is associated with the frequency of said plurality of frequencies, and the second value of each pair is associated with each other frequency for all other frequencies of the analysis frequency range other than the frequency of said plurality of frequencies associated with said pair set, said first value associated with said second change data for the frequency of said plurality of frequencies associated with said pair set, said second value associated with said second change data for each other frequency for all other frequencies of the analysis frequency range other than the frequency of said plurality of frequencies associated with said pair set;
   (x) scoring each of said pair of each of said pair set of each of said action with a pair score;
   (xi) assigning a match value to each of said pair of each of said pair set of each of said action based on a comparison of the pair score of said pair and said baseline value of the frequency of said plurality of frequencies associated with the pair set;
   (xii) for each of said pair set of each of said action summing the match values of each of said pair of said pair set to create a total match value;
   (xiii) for each of said action summing the total match values of each of said pair set of said action to generate a combined match value; and
   (xiv) comparing the combined match value of each of said actions of said second set of actions to the combined match value of each of said actions of said first set of actions to determine whether each of the actions of said second set of actions performed by the subject is true.

2. A method according to claim 1, wherein said match value is one.

3. A method according to claim 1, wherein said determining the baseline value further comprises the steps of:
   (xv) creating a plurality of baseline pair sets for each of said frequency of said plurality of frequencies in said analysis frequency range, each baseline pair set of the plurality of baseline pair sets including a baseline pair, the baseline pair including a first baseline value and a second baseline value the first baseline value of each baseline pair is associated with the frequency of said plurality of frequencies, and the second baseline value of each baseline pair is associated with each other frequency for all other frequencies of the analysis frequency range other than the frequency of said plurality of frequencies associated with said baseline pair set, said first baseline value associated with said first change data for the frequency of said plurality of frequencies in said analysis frequency range associated with said baseline pair set, said second baseline value associated with said first change data for each other frequency for all other frequencies of the analysis frequency range other than the frequency of said plurality of frequencies associated with said baseline pair set;
   (xvi) scoring each of said baseline pair with a positive baseline pair score or negative baseline pair score;
   (xvii) assigning a first frequency baseline value to each of said frequencies of said plurality of frequencies in said analysis frequency range for which a quantity of said positive baseline pair scores is equal to or exceeds a predetermined percentage as the positive baseline pair score;
   (xiii) assigning a second frequency baseline value to each of said frequencies of said plurality of frequencies in said analysis frequency range for which said quantity of said positive baseline pair scores is less than said predetermined percentage as the negative baseline pair score; and (xiv) wherein the baseline pair score forms the baseline value for each frequency of said plurality of frequencies in the analysis frequency range.

4. A method according to claim 1 further comprising the step of:

for each of said action in said first set of actions, plotting said combined match value to create a truth scale.

5. A method according to claim 1 wherein the first and second epochs have a duration of approximately one second.

6. A method according to claim 1 wherein the analysis frequency range is approximately two hertz to approximately one hundred sixty hertz.

* * * * *